United States Patent
Shimokawa et al.

(10) Patent No.: US 10,836,692 B2
(45) Date of Patent: Nov. 17, 2020

(54) METHOD FOR ISOLATING HFC-245CB AND (E)-HFO-1234ZE FROM COMPOSITION CONTAINING BOTH COMPOUNDS

(71) Applicant: DAIKIN INDUSTRIES, LTD., Osaka (JP)

(72) Inventors: Mana Shimokawa, Osaka (JP); Tatsuya Takakuwa, Osaka (JP); Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/527,039

(22) PCT Filed: Nov. 12, 2015

(86) PCT No.: PCT/JP2015/081898
§ 371 (c)(1),
(2) Date: May 16, 2017

(87) PCT Pub. No.: WO2016/080283
PCT Pub. Date: May 26, 2016

(65) Prior Publication Data
US 2017/0320798 A1    Nov. 9, 2017

(30) Foreign Application Priority Data

Nov. 17, 2014  (JP) .................................. 2014-232498

(51) Int. Cl.
*C07C 17/386*      (2006.01)
*B01D 3/40*        (2006.01)

(52) U.S. Cl.
CPC ............... *C07C 17/386* (2013.01); *B01D 3/40* (2013.01)

(58) Field of Classification Search
CPC ....... C07C 17/386; C07C 19/08; C07C 21/18; B01D 3/40
See application file for complete search history.

(56) References Cited

U.S. PATENT DOCUMENTS

| | | | |
|---|---|---|---|
| 5,874,657 A * | 2/1999 | Miller | C07C 17/386 570/178 |
| 6,179,967 B1 | 1/2001 | Nishimura et al. | |
| 2011/0201851 A1* | 8/2011 | Nose | C07C 17/087 570/154 |
| 2011/0270001 A1 | 11/2011 | Ishihara et al. | |
| 2012/0041239 A1* | 2/2012 | Suzuki | C07C 17/206 570/160 |
| 2013/0105296 A1* | 5/2013 | Chaki | C01B 7/196 203/60 |

FOREIGN PATENT DOCUMENTS

| | | |
|---|---|---|
| JP | 7-133240 | 5/1995 |
| JP | 11-43451 | 2/1999 |
| JP | 2010-202640 | 9/2010 |
| JP | 2012-524026 | 10/2012 |
| JP | 2013-521275 | 6/2013 |
| WO | 2010/090086 | 8/2010 |
| WO | 2010/123154 | 10/2010 |
| WO | 2012/011609 | 1/2012 |

OTHER PUBLICATIONS

International Search Report dated Feb. 2, 2016 in International (PCT) Application No. PCT/JP2015/081898.
Extended European Search Report dated May 4, 2018 in European Application No. 15862093.0.

* cited by examiner

*Primary Examiner* — Derek N Mueller
(74) *Attorney, Agent, or Firm* — Wenderoth, Lind & Ponack, L.L.P.

(57) ABSTRACT

The present invention provides a method for separating HFC-245cb and (E)-HFO-1234ze having close boiling points, i.e., boiling points with only 1° C. difference, by extractive distillation from a composition containing the HFC-245cb and the (E)-HFO-1234ze. More specifically, the present invention is a method for separating HFC-245cb and (E)-HFO-1234ze from a composition containing the HFC-245cb and the (E)-HFO-1234ze, the method comprising subjecting the composition to extractive distillation using at least one extractant selected from the group consisting of halogenated hydrocarbons, halogenated unsaturated hydrocarbons, nitriles, ketones, carbonates, alcohols, hydrocarbons, esters and ethers.

4 Claims, No Drawings

US 10,836,692 B2

METHOD FOR ISOLATING HFC-245CB AND (E)-HFO-1234ZE FROM COMPOSITION CONTAINING BOTH COMPOUNDS

TECHNICAL FIELD

The present invention relates to a method for separating HFC-245cb and (E)-HFO-1234ze from a composition containing HFC-245cb (1,1,1,2,2-pentafluoropropane) and (E)-HFO-1234ze ((E)-1,3,3,3-tetrafluoropropene) having close boiling points.

BACKGROUND ART

Hydrofluorocarbons, such as HFC-125 (pentafluoroethane), HFC-32 (difluoroethane), and the like, have been used as alternative refrigerants to replace chlorine-based refrigerants. However, in the field of refrigerants, the use of a substance that has less of an effect on global warming has been desired.

As alternative refrigerants satisfying the above demands, natural (non-Freon) refrigerants, such as $CO_2$, isobutane, and the like, have been considered. However, since $CO_2$ refrigerants must be used under conditions of high temperature and high pressure, compared with Freon-based refrigerants, the device size increases, thereby increasing energy consumption. The $CO_2$ refrigerants thus cause many problems. Further, hydrocarbon-based substances such as isobutane are highly combustible and therefore unfavorable in terms of safety.

In recent years, as a substance that can solve such drawbacks, HFO-1234yf (2,3,3,3-tetrafluoropropene, boiling point −29.4° C.), which is a fluorine-containing unsaturated hydrocarbon having a low global warming potential, has attracted attention as an alternative refrigerant. HFO-1234yf is obtained, for example, by a gas phase fluorination reaction of HCFC-1233xf (2-chloro-3,3,3-trifluoro propene). In this reaction, HFC-245cb (boiling point=−18.3° C.) is produced as a by-product together with HFO-1234yf. Since HFC-245cb and HFO-1234yf are in equilibrium with each other, by separating and collecting HFC-245cb, and recycling it in the gas phase fluorination reaction, it is possible to increase the yield of HFO-1234yf, which is the desired product. Further, in addition to HFO-1234yf, (E)-HFO-1234ze (boiling point=−19.0° C.), which is an isomer, is also produced as a by-product in the gas phase fluorination reaction. This compound may be used for various purposes, such as refrigerants (including heating media; the same hereinafter), foaming agents, aerosol propellants, solvents, cleaning agents, fire extinguishers, and polymerization solvents.

Generally, in industrial purification methods, a distillation method is used to separate a liquid or a liquefiable gas mixture. However, when impurities having a boiling point close to the boiling point of the desired product to be separated are contained, it is difficult to separate the desired product from the impurities. Therefore, for a system in which separation by general distillation is difficult, so-called extractive distillation methods have been performed, in which distillation is performed using, as the third component, an extraction solvent that selectively changes relative volatility (specific volatility).

Patent Document 1 is an example of a prior art document relating to an extractive distillation method. Patent Document 1 discloses performing extractive distillation of a mixture containing (Z)-HCFO-1233zd ((Z)-1-chloro-3,3,3-trifluoropropene, boiling point=39.0° C.) and HCFC-244fa (1-chloro-1,3,3,3-tetrafluoropropane, boiling point=42.2° C.) in the presence of, as an extraction solvent, at least one kind selected from a specific halogenated hydrocarbon, halogenated unsaturated hydrocarbons, nitriles, ketones, carbonates, ethers, esters, and alcohols.

CITATION LIST

Patent Documents

Patent Document 1: JP2010-202640A

SUMMARY OF INVENTION

Technical Problem

As described above, in the gas phase fluorination reaction of HCFC-1233xf, the desired product, i.e., HFO-1234yf is obtained as a mixture with HFC-245cb, which is in equilibrium with HFO-1234yf. Since the boiling points of HFO-1234yf and HFC-245cb in a normal state are −29.4° C. and −18.3° C., respectively, these compounds may be easily separated by a typical distillation method using the boiling point difference.

However, if (E)-HFO-1234ze is contained together with HFC-245cb, since the boiling points of these compounds are very close, namely, −19.0° C. and −18.3° C., respectively, the separation is difficult by a general distillation method because an attempt to separate one inevitably causes separation of the other. The separation of HFC-245cb and (E)-HFO-1234ze has thus been problematic because they cannot be easily separated by a general distillation method.

In the industrial use of extractive distillation, the selection of the extraction solvent is most important. It is also important to optimize the distillation conditions for each extraction solvent to be used. Patent Document 1 mentioned above discloses the separation of HCFC-244fa, which has a structure similar to that of HFC-245cb, and (Z)-HCFO-1233zd, which has a structure similar to that of (E)-HFO-1234ze by extractive distillation. Although HCFC-244fa and (Z)-HCFO-1233zd have close boiling points, since the boiling point difference is 3° C. or more, they can be separated by extractive distillation relatively easily.

In contrast, the boiling point difference between HFC-245cb and (E)-HFO-1234ze is only 1° C. Therefore, the conditions regarding the possibility of separating these compounds are significantly severe compared with the conditions disclosed in Patent Document 1. Thus, it is impossible to predict from the disclosure of Patent Document 1 the possibility of separation of HFC-245cb and (E)-HFO-1234ze.

The present invention was completed in light of such a problem, and an object of the present invention is to provide a method of separating HFC-245cb and (E)-HFO-1234ze having close boiling points, i.e., boiling points with only 1° C. difference, from a composition containing HFC-245cb and (E)-HFO-1234ze by extractive distillation.

Solution to Problem

The inventors of the present invention conducted extensive research regarding a method for separating HFC-245cb and (E)-HFO-1234ze having close boiling points, i.e., boiling points with only 1° C. difference, from a composition containing HFC-245cb and (E)-HFO-1234ze, and found that the object can be attained by extractive distillation using a specific extraction solvent. With this finding, the inventors completed the present invention.

Specifically, the present invention relates to the following methods for separating HFC-245cb and (E)-HFO-1234ze.
1. A method for separating HFC-245cb and (E)-HFO-1234ze from a composition comprising the HFC-245cb and the (E)-HFO-1234ze, the method comprising subjecting the composition to extractive distillation in the presence of at least one extraction solvent selected from the group consisting of halogenated hydrocarbons, halogenated unsaturated hydrocarbons, nitriles, ketones, carbonates, alcohols, hydrocarbons, esters, and ethers.
2. The method according to Item 1, wherein the extraction solvent has a normal boiling point ranging from 30° C. to 100° C.
3. The method according to Item 1 or 2, wherein the extraction solvent is at least one member selected from the group consisting of carbon tetrachloride, acetonitrile, acetone, dimethyl carbonate, ethanol, and n-hexane.

Advantageous Effects of Invention

The separation method of the present invention enables the separation of HFC-245cb and (E)-HFO-1234ze having close boiling points, i.e., boiling pointes with only 1° C. difference, by performing extractive distillation in the presence of a specific extraction solvent. By enabling such separation, HFC-245cb may be recycled in a reaction for producing HFO-1234yf (for example, a gas phase fluorination reaction of HCFC-1233xf). Further, (E)-HFO-1234ze can be used for various useful purposes such as refrigerants, foaming agents, aerosol propellants, solvents, cleaning agents, fire extinguishers, polymerization solvents, and the like.

DESCRIPTION OF EMBODIMENTS

The present invention is a method for separating HFC-245cb and (E)-HFO-1234ze from a composition containing HFC-245cb and (E)-HFO-1234ze, the method comprising subjecting the composition to extractive distillation in the presence of at least one extraction solvent selected from the group consisting of halogenated hydrocarbons, halogenated unsaturated hydrocarbons, nitriles, ketones, carbonates, alcohols, hydrocarbons, esters, and ethers.

The separation method of the present invention having the features described above enables the separation of HFC-245cb and (E)-HFO-1234ze having close boiling points, i.e., boiling pointes with only 1° C. difference, by performing extractive distillation in the presence of a specific extraction solvent. By enabling such separation, HFC-245cb may be recycled in a reaction for producing HFO-1234yf (for example, a gas phase fluorination reaction of HCFC-1233xf). Further, (E)-HFO-1234ze can be used for various useful purposes such as refrigerants, foaming agents, aerosol propellants, solvents, cleaning agents, fire extinguishers, polymerization solvents, and the like.

The composition containing HFC-245cb and (E)-HFO-1234ze to which the extractive distillation of the present invention can be applied is not limited insofar as the composition contains the two compounds. Examples include compositions obtained after the production of HFO-1234yf by a gas phase fluorination reaction of HCFC-1233xf.

The formulation of the composition obtained after the above reaction varies depending on the reaction conditions or the distillation purification conditions during the production of HFO-1234yf; however, due to chemical equilibrium, the formulation of the composition obtained after the reaction becomes constant according to parameters such as reaction temperature, pressure, or purification distillation. Generally, the conditions are set so that the production efficiency of HFO-1234yf becomes maximum or the production cost becomes minimum.

The formulation of the composition to which the extractive distillation of the present invention can be applied is not particularly limited; however, the molar ratio of (E)-HFO-1234ze to HFC-245cb is such that the molar amount of HFC-245cb is preferably 0.1 to 50 mol, and more preferably about 1 to 30 mol, per mole of (E)-HFO-1234ze.

The means for obtaining the composition to which the extractive distillation of the present invention can be applied is not limited to the gas phase fluorination reaction of HCFC-1233xf. For example, a method for producing fluoroolefin that includes, as its concept, the gas phase fluorination reaction of HCFC-1233xf, may be used as a means for producing the composition.

More specifically, as the means, it is possible to adopt a process for producing a fluoroolefin represented by formula (6): $CF_3(CF_2)_nCA=CHB$, wherein one of A and B is F and the other is H, n is an integer of 0 to 2, with the proviso that n is 0 when a chlorine-containing alkene represented by formula (5) is used as a starting material, the process comprising reacting, in a gas phase, a fluorinating agent and at least one chlorine-containing compound in the presence of at least one catalyst selected from the group consisting of chromium oxide containing a Group 5 element and fluorinated chromium oxide containing a Group 5 element, the at least one chlorine-containing compound being selected from the group consisting of a chlorine-containing alkane represented by formula (1): $CX_3(CX_2)_nCCIYCH_2Z$, wherein X is independently F or Cl, Y is H or F, when Y is H, Z is Cl or F, and when Y is F, Z is H, and n is an integer of 0 to 2; a chlorine-containing alkane represented by formula (2): $CX_3(CX_2)_nCH_2CHX_2$, wherein X is independently F or Cl, and at least one X is Cl, and n is an integer of 0 to 2; a chlorine-containing alkene represented by formula (3): $CX_3(CX_2)_nCCI=CH_2$, wherein X is independently F or Cl, and n is an integer of 0 to 2; a chlorine-containing alkene represented by formula (4): $CX_3(CX_2)_nCH=CHX$, wherein X is independently F or Cl, and at least one X is Cl, and n is an integer of 0 to 2; and a chlorine-containing alkene represented by formula (5): $CH_2XCCl=CX_2$, wherein X is independently F or Cl.

Distillation separation of HFC-245cb and (E)-HFO-1234ze may be accomplished by increasing or decreasing the relative volatility of these compounds from 1.

The relative volatility is defined as a ratio of equilibrium factors of constituents of the fluid mixture. When the constituents are (E)-HFO-1234ze (A) and HFC-245cb (B), the relative volatility of (E)-HFO-1234ze (A) to HFC-245cb (B) (A/B) is expressed as follows.

Relative volatility $(A/B)=X/Y$

X represents "gas phase mole fraction/liquid phase mole fraction" regarding A.

Y represents "gas phase mole fraction/liquid phase mole fraction" regarding B.

The extraction solvent used for the present invention is a substance that can change the relative volatility of (E)-HFO-1234ze (A) to HFC-245cb (B).

To distil (E)-HFO-1234ze, generally, an extraction solvent ensuring a relative volatility of more than 1, and preferably a relative volatility of 2 or more, is preferably used. When the relative volatility is more than 1, the gas phase mole fraction of (E)-HFO-1234ze increases; therefore, (E)-HFO-1234ze in the gas phase increases, thereby enabling separation by distillation.

In contrast, to distil HFC-245cb, an extraction solvent ensuring a relative volatility of less than 1 is preferably used. When the relative volatility is less than 1, the liquid phase mole fraction of (E)-HFO-1234ze increases; therefore, (E)-HFO-1234ze in the liquid phase increases, thereby enabling distillation of HFC-245cb.

In the present invention, it is preferable to use an extraction solvent that can be easily separated from the substance to be extracted, i.e., HFC-245cb.

When the relative volatility is 1, the formulations of all phases become equivalent; as a result, separation by distillation cannot be performed.

The separation method of the present invention uses at least one kind of extraction solvent selected from the group consisting of halogenated hydrocarbons, halogenated unsaturated hydrocarbons, nitriles, ketones, carbonates, alcohols, hydrocarbons, esters, and ethers.

Specific examples of halogenated hydrocarbons usable as extraction solvent include 1,1-dichloro-3,3,3-trifluoro propane, 1,1,3-trichloro-3,3-difluoro propane, 1,1,2-trichloro-3,3,3-trifluoro propane, 1,1,1,3,3-pentachloro propane, and carbon tetrachloride. Among these, carbon tetrachloride is preferable.

Examples of halogenated unsaturated hydrocarbons include 1,2-dichloro-3,3,3-trifluoro propene, 1,2,3-trichloro-3,3-difluoro propene, 1,2,3,3-tetra chloro-3-fluoro propene, 1,3-dichloro-3,3-difluoro propene, 2,3-dichloro-3,3-difluoro propene, 1,3,3-trichloro-3-fluoro propene, and 2,3,3-trichloro-3-fluoro propene.

Examples of nitriles include acetonitrile, propionitrile, and butyronitrile. Among these, acetonitrile is preferable.

Examples of ketones include acetone, methyl ethyl ketone, methyl isobutyl ketone, diethyl ketone, acetylacetone, and cyclo hexanone. Among these, acetone is preferable.

Examples of carbonates include dimethyl carbonate, diethyl carbonate, dipropyl carbonate and dibutyl carbonate. Among these, dimethyl carbonate is preferable.

Examples of alcohols include methanol, ethanol, isopropanol, butanol, 2,2,3,3-tetra fluoro propanol, and 1-(trifluoro methyl)-2,2,2-trifluoro ethanol. Among these, ethanol is preferable.

Examples of hydrocarbons include n-pentane, i-pentane, and n-hexane. Among these, n-hexane is preferable.

Examples of esters include methyl acetate, ethyl acetate, propyl acetate, butyl acetate, trimethyl orthoformate, dimethyl sulfate, and γ-butyrolactone.

Examples of ether include dipropyl ether, dibutyl ether, tetrahydrofuran, tetrahydropyran, 1,3-dioxolan, and 1,4-dioxane.

These extraction solvents can be used singly or as a mixture of two or more kinds.

Further, if the solvents are water-soluble, they may be used as extraction solvents by being mixed with water. For example, aqueous solutions of acetone, acetonitrile, methanol, ethyl acetate, and the like, may be used. In view of extraction efficiency, the mixed ratio of the organic compound and water is preferably such that the water is less than 50 mass %.

Regarding the temperature range of the normal boiling point of the extraction solvent, it is preferable to ensure a temperature difference to the extent that the extraction solvent and the compound to be separated of the present invention can be separated by simple distillation, stripping, or the like, i.e., generally, a temperature difference of 20° C. or more. However, if the normal boiling point is excessively high, decomposition of the extraction solvent itself may occur. Therefore, the range of the normal boiling point of the extraction solvent is preferably about 30 to 150° C., and more preferably about 30 to 80° C.

The amount of the extraction solvent to be used in the separation method of the present invention is not particularly limited, and it is more efficient to use the extraction solvent in an amount greater than that of the raw material (a composition containing HFC-245cb and (E)-HFO-1234ze) (i.e., the concentration of the extraction solvent is higher). However, if the proportion of the extraction solvent is excessively high, it is not economically preferable because it results in an increase in the size of the device or an increase in utility; in contrast, if the proportion of the extraction solvent is excessively low, it is not preferable because the separation effect decreases and the product purity cannot be increased. Therefore, for example, the amount of the extraction solvent is preferably 10 to 10000 parts by mass, more preferably 50 to 5000 parts by mass, and most preferably 100 to 2000 parts by mass, per 100 parts by mass of the raw material (the composition containing HFC-245cb and (E)-HFO-1234ze).

The separation method of the present invention may be performed by using a distillation column. It is preferable to use a packed column or a plate column. The extraction solvent is preferably introduced from a stage above the stage for supplying the raw material so that the extraction solvent is present in the entire distillation column. The number of stages between the stage for introducing the extraction solvent and the stage for supplying the raw material, and the number of stages between the top column and the stage for introducing the extraction solvent, and the number of stages between the bottom column and the stage for supplying the raw material are suitably selected based on preliminary consideration of the relationship between the purity of distillate components, the recovery rate, and the like.

When an extraction solvent with a relative volatility of more than 1 is used, extractive distillation is performed by distilling (E)-HFO-1234ze from the top column, and collecting the extraction solvent and HFC-245cb in a distillation still. Operating conditions such as the temperature at each portion of the distillation column, the stages for supplying the raw material, and the supply amount of the extraction solvent are not particularly limited; they differ depending on the performance of the distillation column, the content ratio of (E)-HFO-1234ze to HFC-245cb in the target substance to be treated (raw material), the type and amount of the extraction solvent to be used, and the like. These conditions may be determined by a preliminary test. Further, to ensure the stability of the distillation operation, it is possible to add an extraction solvent to the raw material. The method of the present invention may be performed as a discontinuous operation or a continuous operation. A continuous operation is industrially preferable. Further, by repeating the extractive distillation, the distillate component can be highly purified.

As the reactor of the present invention, a reactor made of carbon steel with an inner face lined with at least one member selected from glass, stainless-steel, tetrafluoride ethylene resin, chloro trifluoro ethylene resin, polyvinylidene fluoride, PFA resin, and the like, can be suitably used.

EXAMPLES

The present invention is specifically described below with reference to Examples and Comparative Examples. However, the present invention is not limited to these Examples. In the Examples below, the efficacy as the extraction solvent was evaluated based on the relative volatility of (E)-HFO-1234ze to HFC-245cb.

Method for Measuring Relative Volatility (E)-HFO-1234ze, HFC-245cb, and an extraction solvent in amounts shown in Table 1 were placed in a sampling gas cylinder. While remaining still, the body of the sampling gas cylinder was heated for 3 hours.

Thereafter, the molar ratio of HFC-245cb and (E)-HFO-1234ze was measured from the measurement of the pressure inside the sampling gas cylinder and the results of gas chromatography analysis of a gas obtained from the gas phase, thereby determining the relative volatility of (E)-HFO-1234ze to HFC-245cb.

Example 1 (Extractant: Acetone)

2.68 g of (E)-HFO-1234ze, 0.58 g of HFC-245cb, and 55.23 g of acetone were placed in a sampling gas cylinder, and the liquid phase temperature was set to 20° C. As a result, the pressure became 0.04 MPaG (gauge pressure).

After maintaining the conditions for at least 3 hours, the gas phase was obtained and analyzed by gas chromatography. The relative volatility of (E)-HFO-1234ze to HFC-245cb was 0.43. Table 1 shows the amounts, conditions of extractive distillation, and relative volatility.

Example 2 (Extractant: Acetonitrile)

13.91 g of (E)-HFO-1234ze, 3.04 g of HFC-245cb, and 38.66 g of acetonitrile were placed in a sampling gas cylinder, and the liquid phase temperature was set to 20° C. As a result, the pressure became 0.06 MPaG (gauge pressure).

After maintaining the conditions for at least 3 hours, the gas phase was obtained and analyzed by gas chromatography. The relative volatility of (E)-HFO-1234ze to HFC-245cb was 0.52. Table 1 shows the amounts, conditions of extractive distillation, and relative volatility.

Example 3 (Extractant: Dimethyl Carbonate)

12.32 g of (E)-HFO-1234ze, 2.69 g of HFC-245cb, and 85.33 g of dimethyl carbonate were placed in a sampling gas cylinder, and the liquid phase temperature was set to 20° C. As a result, the pressure became 0.05 MPaG (gauge pressure).

After maintaining the conditions for at least 3 hours, the gas phase was obtained and analyzed by gas chromatography. The relative volatility of (E)-HFO-1234ze to HFC-245cb was 0.59. Table 1 shows the amounts, conditions of extractive distillation, and relative volatility.

Example 4 (Extractant: Ethanol)

11.74 g of (E)-HFO-1234ze, 4.09 g of 245cb, and 33.59 g of ethanol were placed in a sampling gas cylinder, and the liquid phase temperature was set to 20° C. As a result, the pressure became 0.23 MPaG (gauge pressure).

After maintaining the conditions for at least 3 hours, the gas phase was obtained and analyzed by gas chromatography. The relative volatility of (E)-HFO-1234ze to HFC-245cb was 0.57. Table 1 shows the amounts, conditions of extractive distillation, and relative volatility.

Example 5 (Extractant: Carbon Tetrachloride)

12.20 g of (E)-HFO-1234ze, 5.57 g of HFC-245cb, and 113.59 g of carbon tetrachloride were placed in a sampling gas cylinder, and the liquid phase temperature was set to 20° C. As a result, the pressure became 0.21 MPaG (gauge pressure).

After maintaining the conditions for at least 3 hours, the gas phase was obtained and analyzed by gas chromatography. The relative volatility of (E)-HFO-1234ze to HFC-245cb was 0.76. Table 1 shows the amounts, conditions of extractive distillation, and relative volatility.

Example 6 (Extractant: N-Hexane)

12.69 g of (E)-HFO-1234ze, 4.61 g of HFC-245cb, and 64.29 g of n-hexane were placed in a sampling gas cylinder, and the liquid phase temperature was set to 20° C. As a result, the pressure became 0.20 MPaG (gauge pressure).

After maintaining the conditions for at least 3 hours, the gas phase was obtained and analyzed by gas chromatography. The relative volatility of (E)-HFO-1234ze to HFC-245cb was 0.77. Table 1 shows the amounts, conditions of extractive distillation, and relative volatility.

Comparative Example 1 (Extraction Solvent Was Not Used)

30.16 g of (E)-HFO-1234ze and 6.59 g of HFC-245cb were placed in a sampling gas cylinder, and the liquid phase temperature was set to 20° C. As a result, the pressure became 0.31 MPaG (gauge pressure).

After maintaining the conditions for at least 3 hours, the gas phase was obtained and analyzed by gas chromatography. The relative volatility of (E)-HFO-1234ze to HFC-245cb was 1.01. Table 1 shows the amounts, conditions of extractive distillation, and relative volatility.

TABLE 1

| | | Amount (g) | | | | | | |
| --- | --- | --- | --- | --- | --- | --- | --- | --- |
| | Extraction Solvent | 1234ze | 245cb | Extraction Solvent | Temperature (° C.) | Pressure (MPaG) | Time (h) | Relative volatility |
| Example 1 | Acetone | 2.68 | 0.58 | 55.23 | 20 | 0.04 | >3 | 0.43 |
| Example 2 | Acetonitrile | 13.91 | 3.04 | 38.66 | 20 | 0.06 | >3 | 0.52 |
| Example 3 | Dimethyl carbonate | 12.32 | 2.69 | 85.33 | 20 | 0.05 | >3 | 0.59 |
| Example 4 | Ethanol | 11.74 | 4.09 | 33.59 | 20 | 0.23 | >3 | 0.57 |
| Example 5 | Carbon tetrachloride | 12.20 | 5.57 | 113.53 | 20 | 0.21 | >3 | 0.76 |

TABLE 1-continued

| | Extraction Solvent | Amount (g) | | | Temperature (° C.) | Pressure (MPaG) | Time (h) | Relative volatility |
| --- | --- | --- | --- | --- | --- | --- | --- | --- |
| | | 1234ze | 245cb | Extraction Solvent | | | | |
| Example 6 | n-hexane | 12.69 | 4.61 | 64.29 | 20 | 0.20 | >3 | 0.77 |
| Comparative Example 1 | — | 30.16 | 6.59 | — | 20 | 0.31 | >3 | 1.01 |

The results shown in Table 1 clearly reveal that, in Comparative Example 1 (extraction solvent was not used), since the boiling points of (E)-HFO-1234ze and HFC-245cb were close, and the relative volatility was 1.01, separation by general distillation was difficult, and that, in contrast, in Examples 1 to 6 (extraction solvent was used), the relative volatility fell in a range of 0.43 to 0.77, and separation of (E)-HFO-1234ze and HFC-245cb by extractive distillation was possible. Although it technically depends on the relationship with the operation conditions of the distillation device, generally, separation by extractive distillation can be suitably performed, when the relative volatility is less than 1, in a range of 0.2 to 0.8 (more preferably between 0.4 to 0.8), and, when the relative volatility is more than 1, in a range of 1.2 to 3.0 (more preferably between 1.2 to 2.1).

The invention claimed is:

1. A method for separating HFC-245cb and (E)-HFO-1234ze from a composition comprising the HFC-245cb and the (E)-HFO-1234ze, the method comprising subjecting the composition to extractive distillation in the presence of at least one extraction solvent selected from the group consisting of 1,1-dichloro-3,3,3-trifluoro propane, 1,1,3-trichloro-3,3-difluoro propane, 1,1,2-trichloro-3,3,3-trifluoro propane, 1,1,1,3,3-pentachloro propane, carbon tetrachloride, acetonitrile, propionitrile, butyronitrile, acetone, methyl ethyl ketone, methyl isobutyl ketone, diethyl ketone, acetylacetone, cyclo hexanone, dimethyl carbonate, diethyl carbonate, dipropyl carbonate, dibutyl carbonate, methanol, ethanol, isopropanol, butanol, 2,2,3,3-tetra fluoro propanol, 1-(trifluoro methyl)-2,2,2-trifluoro ethanol, n-pentane, i-pentane, and n-hexane, thus separating the HFC-245cb and the (E)-HFO-1234ze from the composition comprising the HFC-245cb and the (E)-HFO-1234ze,
wherein relative volatility (AB) of (E)-HFO-1234ze (A) to HFC-245cb (B) of the separated HFC-245cb and (E)-HFO-1234ze is less than 1, and
wherein the molar ratio of HFC-245cb to (E)-HFO-1234ze in the composition is 50 or less.

2. The method according to claim 1, wherein the extraction solvent has a normal boiling point ranging from 30° C. to 100° C.

3. The method according to claim 1, wherein the extraction solvent is at least one member selected from the group consisting of carbon tetrachloride, acetonitrile, acetone, dimethyl carbonate, ethanol and n-hexane.

4. The method according to claim 2, wherein the extraction solvent is at least one member selected from the group consisting of carbon tetrachloride, acetonitrile, acetone, dimethyl carbonate, ethanol and n-hexane.

* * * * *